United States Patent
Jeon et al.

(10) Patent No.: US 9,719,989 B2
(45) Date of Patent: Aug. 1, 2017

(54) METHOD FOR DETECTING FOOD POISONING BACTERIA USING MAGNETIC NANOPARTICLES AND SOLUTION HAVING HIGH VISCOSITY

(71) Applicants: POSTECH ACADEMY-INDUSTRY FOUNDATION, Pohang-si (KR); REPUBLIC OF KOREA (MINISTER OF FOOD AND DRUG SAFETY), Cheongwon-gun (KR)

(72) Inventors: Sangmin Jeon, Pohang-si (KR); Dong-hoon Kwon, Busan (KR); Jin myoung Joo, Busan (KR); Ki hwan Park, Seoul (KR); Sang-Bae Han, Seoul (KR); Hwa-Jung Lee, Seoul (KR); Kyu-Heon Kim, Asan-si (KR)

(73) Assignees: POSTECH ACADEMY-INDUSTRY FOUNDATION, Pohang-si, Gyeongsangbuk-Do (KR); REPUBLIC OF KOREA (MINISTER OF FOOD AND DRUG SAFETY), Chungcheongbuk-Do (KR)

( * ) Notice: Subject to any disclaimer, the term of this patent is extended or adjusted under 35 U.S.C. 154(b) by 0 days.

(21) Appl. No.: 14/646,984

(22) PCT Filed: Nov. 26, 2013

(86) PCT No.: PCT/KR2013/010765
§ 371 (c)(1),
(2) Date: May 22, 2015

(87) PCT Pub. No.: WO2014/081265
PCT Pub. Date: May 30, 2014

(65) Prior Publication Data
US 2015/0293083 A1 Oct. 15, 2015

(30) Foreign Application Priority Data
Nov. 26, 2012 (KR) .......................... 10-2012-0134544

(51) Int. Cl.
G01N 33/53 (2006.01)
G01N 33/543 (2006.01)
C12Q 1/04 (2006.01)
C12Q 1/24 (2006.01)
G01N 33/58 (2006.01)
G01N 33/569 (2006.01)

(52) U.S. Cl.
CPC ......... *G01N 33/54333* (2013.01); *C12Q 1/04* (2013.01); *C12Q 1/24* (2013.01); *G01N 33/54326* (2013.01); *G01N 33/54346* (2013.01); *G01N 33/56911* (2013.01); *G01N 33/56916* (2013.01); *G01N 33/587* (2013.01); *G01N 2333/255* (2013.01)

(58) Field of Classification Search
None
See application file for complete search history.

(56) References Cited

U.S. PATENT DOCUMENTS

| | | |
|---|---|---|
| 5,279,936 A | 1/1994 | Vorpahl |
| 2010/0109653 A1 | 5/2010 | Nieuwenhuis et al. |
| 2011/0262926 A1 | 10/2011 | Esch et al. |

FOREIGN PATENT DOCUMENTS

| | | |
|---|---|---|
| KR | 1020110006334 A | 1/2011 |
| WO | 00-42410 A1 | 7/2000 |

OTHER PUBLICATIONS

Qiu et al. Advanced Materials 2011 vol. 23, p. 4880-4885.*
Matsunaga et al. (Analytical Chem Acta 2007 vol. 597, p. 331-339).*
International Search Report for PCT/KR2013/010765 mailed Mar. 19, 2014 (Mar. 19, 2014); the whole document.
Jun Hu et al: "A multicomponent recognition and separation system established via fluorescent, magnetic, dualencoded multifunctional bioprobes"; Biomaterials, 32, vol. 32, Issue 4, Feb. 2011, pp. 1177-1184, the whole document.

* cited by examiner

*Primary Examiner* — Jacob Cheu
(74) *Attorney, Agent, or Firm* — Steptoe & Johnson LLP

(57) ABSTRACT

The present invention relates to a method for detecting food poisoning bacteria, and more particularly, to a method for rapidly and quantitatively isolating food poisoning bacteria contents which contaminate food and the like. The method according to the present invention is characterized by including the steps of: introducing magnetic nanoparticles which can bind to bacteria into a sample for measuring the bacteria so as to bind the magnetic nanoparticles to the bacteria; isolating the magnetic nanoparticles; passing the nanoparticles which are isolated by using magnetism through a solution having high viscosity so as to separate the magnetic nanoparticles to which bacteria are bound from magnetic nanoparticles to which no bacteria are bound; and quantifying the magnetic nanoparticles to which bacteria are bound.

13 Claims, 7 Drawing Sheets

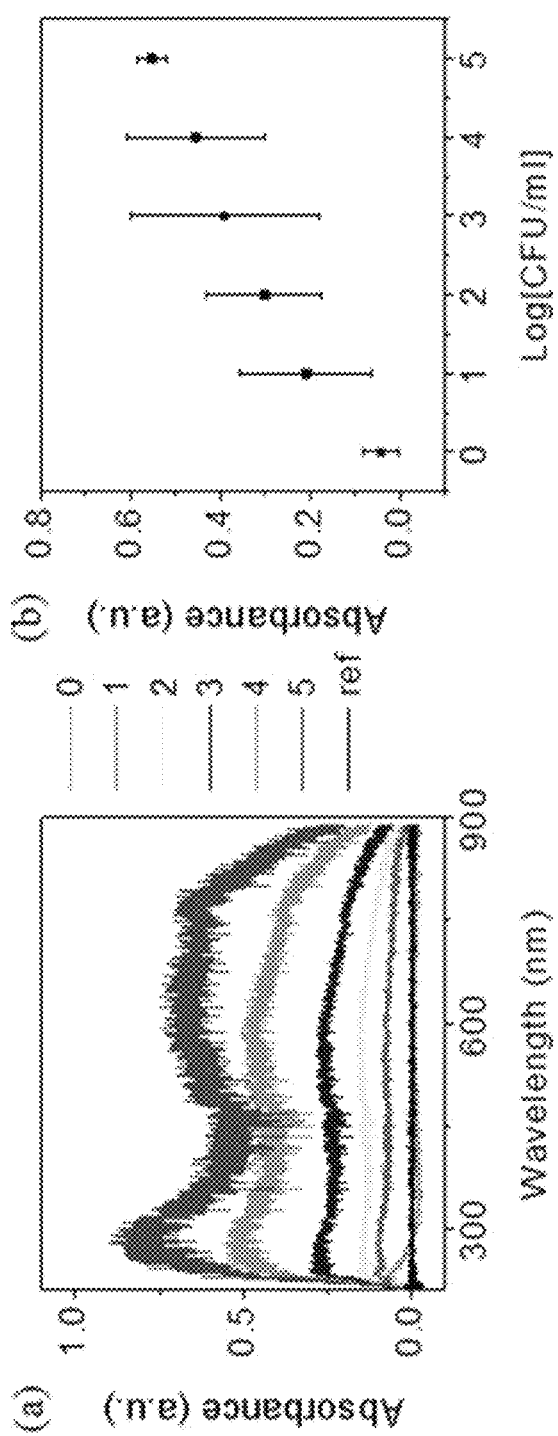

METHOD FOR DETECTING FOOD POISONING BACTERIA USING MAGNETIC NANOPARTICLES AND SOLUTION HAVING HIGH VISCOSITY

CLAIM FOR PRIORITY

This application claims priority under 35 USC 371 to International Application No. PCT/KR2013/010765, filed on Nov. 26, 2013, which claims priority to Korean Patent Application No. 10-2012-0134544, which was filed on Nov. 26, 2012, each of which is hereby incorporated by reference in its entirety.

TECHNICAL FIELD

The present invention relates to a method for detecting food poisoning bacteria and, more particularly, to a method for quantitatively analyzing food poisoning bacteria in a food sample in a rapid manner.

BACKGROUND ART

The number of food poisoning cases has increased with the worldwide increase in agrifood pollution over the past decade. Accordingly, there is increased demand for diagnostic methods for rapidly detecting contamination with food poisoning bacteria in the early stages of food processing/production, preceding the distribution of final food products, thereby preventing the onset of food poisoning and reducing the social cost of food poisoning. Conventionally, food poisoning bacteria are detected by culturing and biochemical assays, but it takes 3~5 days to obtain final diagnostic data, which is too slow to prevent food poisoning incidents in advance of the distribution of food products.

To overcome the above problems, Korea Patent No. 1149418, issued to the Republic of Korea, discloses a method for quantitatively measuring bacterial amounts in which a fluorescent nanoparticle conjugate containing an antibody is added to bacterial mass and allowed to bind to specific bacteria, followed by quantitating the level of a specific bacteria from measurements of fluorescent intensity. To this end, a layer of the biomolecule avidin is formed on fluorescent nanoparticles (quantum dots, QD), and coupled with antibody-conjugated biotin. The resulting conjugate binds to the specific bacteria when the antibody reacts with a specific bacterial antigen.

In addition, *Biomaterials* 32(2011)1177~1184, "A multicomponent recognition and separation system established via fluorescent, magnetic, dualencoded multifunctional bioprobes," issued to Jun ha, et al., discloses a magnetic particle with a size of about 3 micrometers that is conjugated at a terminal carboxylic group with a fluorescent particle and an antibody. The conjugated magnetic particle is allowed to bind to specific bacteria, and is then separated by magnetism.

However, this method has difficulty in effectively separating bacteria-bound particles and non-bound particles, and suffers from the disadvantage that additional fluorescent particles are required for quantitative analysis.

There is therefore a need for a novel method by which bacteria-bound particles can be effectively separated from non-bound particles and can be readily quantitatively analyzed.

DISCLOSURE

Technical Problem

It is an object of the present invention to provide a method for determining the content of bacteria in a sample.

It is another object of the present invention to provide a method for rapidly quantifying bacteria in a sample in which particles bound with bacteria through antigen-antibody interaction can be readily separated from non-bound particles.

Technical Solution

To accomplish the above objects, an aspect of the present invention provides a method for quantitatively analyzing bacteria in a sample, comprising:

introducing magnetic nanoparticles capable of capturing bacteria into the sample and allowing the magnetic nanoparticles to capture bacteria;

enriching the magnetic nanoparticles from the sample;

passing the enriched magnetic nanoparticles through a highly viscous medium in presence of a magnetic field to separate the magnetic nanoparticles into bacterium-complexed magnetic nanoparticles and free magnetic nanoparticles; and quantitating the bacterium-complexed magnetic nanoparticles.

In the present invention, the magnetic nanoparticles may be smaller in size than bacteria, so that one or more nanoparticles bind to one bacterium. In one exemplary embodiment, the magnetic nanoparticles range in size from 1 to 10000 nanometers, preferably from 50 to 1000 nanometers, and more preferably from 100 to 500 nanometers. In another exemplary embodiment, the magnetic nanoparticles may be synthesized using a method well known in the art, or may be commercially available. As used herein, the term "magnetic nanoparticles" refers to nanoparticles that have sufficient magnetic properties to react to magnetism.

In another exemplary embodiment of the present invention, the magnetic nanoparticles may be $Fe_3O_4$ nanoparticles.

No particular limitations are imposed on the bacteria, as long as they can be bound with the magnetic nanoparticles. In one preferred embodiment of the present invention, the bacteria may be food poisoning bacteria that cause illness after foods contaminated with the bacteria are eaten. Examples of food poisoning bacteria include *Salmonella, Staphylococcus, Vibrio, Listeria,* pathogenic *E. coli,* enterohemorrhagic *E. coli* O157, *Campylobacter, Bacillus cereus, Clostridium welchii,* and *Botulinus.*

To be capable of capturing bacteria, the magnetic nanoparticles are provided on a surface or inner site thereof with a bacterium-binding functional entity. In one exemplary embodiment of the present invention, the bacterium-binding functional entity may be an antibody capable of binding to bacteria. A variety of antibodies that can bind to bacteria are known in the art. With regard to the formation of bacterium-binding antibodies on nanoparticles, reference may be made to Jun ha, et al., *Biomaterials* 32(2011)1177~1184, "A multicomponent recognition and separation system established via fluorescent, magnetic, dualencoded multifunctional bioprobes", which is incorporated herein in its entirety by reference. In one exemplary embodiment of the present invention, the bacterium-binding antibodies may be those known in the art.

In the present invention, the capture of bacteria by the magnetic nanoparticles may be implemented through antigen-antibody interaction. A plurality of magnetic nanoparticles may bind to one bacterial particle.

According to the present invention, the magnetic nanoparticles are enriched by magnetism. In this regard, the magnetic nanoparticles, whether complexed with bacteria or not, are enriched together.

When allowed to run in a highly viscous medium in the presence of a magnetic field, the magnetic nanoparticles complexed with bacteria are separated from free nanoparticles because they are different in motility, that is, the distance that they move in a highly viscous medium. Without being bound to a theory, a multitude of magnetic nanoparticles may bind to one food poisoning bacterium, and the resulting food poisoning bacterium-magnetic nanoparticle complex (hereinafter referred to just as "complex") behaves like a very large-sized particle, compared to free magnetic nanoparticles. Accordingly, the complex has a greater magnetic force than do the individual free magnetic nanoparticles. When introduced into a highly viscous medium, the complexes can, therefore, traverse the highly viscous medium faster in the direction of magnetism, compared to the individual free magnetic nanoparticles.

As used herein, the term "highly viscous medium" refers to a liquid having higher viscosity than water under the same conditions. The highly viscous medium suitable for use in the present invention can be determined depending on the magnetism used and the distance the complexes are required to move. In order to separate the magnetic nanoparticles within a short distance, the highly viscous medium is preferably 10- to 1,000-fold higher in viscosity than water, and more preferably 20- to 200-fold higher. By way of example, the medium preferably has a viscosity of about 20~100 mPa·s at room temperature.

In the present invention, the highly viscous medium may be an aqueous polyvinylpyrrolidone solution as disclosed by Chuanbin Mao, et al., *Adv. Mater.* 2011, 23, 4880~4885, "Viscosity Gradient as a Novel Mechanism for the Centrifugation-Based Separation of Nanoparticles," which is incorporated herein in its entirety by reference. For use in the present invention, polyvinylpyrrolidone has a molecular weight of 5,000~30,000, and preferably 6,000~20,000. For example, a solution containing polyvinylpyrrolidone with a molecular weight of about 10,000 in an amount of 10~60 weight % may be used as a highly viscous medium.

In one exemplary embodiment of the present invention, after the bacterium-complexed magnetic nanoparticles and the free magnetic nanoparticles are placed on a highly viscous medium, and then when a magnetic field is applied to the medium from the bottom, the nanoparticles are separated as the complexes move through the medium to the bottom, whereas the free nanoparticles are trapped in a middle position.

In another exemplary embodiment of the present invention, bacterium-complexed magnetic nanoparticles and free magnetic nanoparticles are sucked together into a pipette tip, to which a highly viscous medium is then added so that the nanoparticles are placed on the highly viscous medium. The complexes and the free magnetic nanoparticles can be separated from each other by magnetophoretic chromatography. In this regard, when a permanent magnet is placed underneath the pipette tip, the bacterium-complexed magnetic nanoparticles and the free magnetic nanoparticles move in the medium at different speeds. After the bacterium-complexed magnetic nanoparticles are induced to move sufficiently downward in the presence of a magnetic field, they are withdrawn out of the end of the pipette tip, and thus can be separated from the free magnetic nanoparticles.

As mentioned above, magnetophoretic chromatography using a pipette can separate only the bacterium-complexed magnetic nanoparticles without an additional process of removing free magnetic nanoparticles, and can perform control so as to ensure constant throughput. When using a microtube, the bacterium-complexed magnetic nanoparticles can be isolated only after the free magnetic nanoparticles placed on the highly viscous medium are first removed. Further, the removal of the free magnetic nanoparticles is difficult to conduct to the same degree. In contrast, it is very easy to control the withdrawal of the bacterium-complexed magnetic nanoparticles when using a pipette.

In the present invention, the quantification of the bacterium-complexed magnetic nanoparticles can be achieved by measuring absorbance in a UV-Vis spectrometer.

In accordance with another aspect thereof, the present invention provides a method for separating magnetic nanoparticles, characterized in that magnetic nanoparticles with different magnetism are separated in a highly viscous medium in the presence of a magnetic field.

Advantageous Effects

As described hitherto, the magnetophoresis in which the enrichment of magnetic nanoparticles is carried out in a highly viscous medium in the presence of a magnetic field in accordance with the present invention can discretely separate free magnetic nanoparticles from the bacterium-complexed magnetic nanoparticles, which take a string form in a highly viscous medium. However, a centrifuge, if used, degrades the separation resolution between the complexes and the free magnetic nanoparticles. In addition, the method of the present invention is very advantageous in that no additional equipment, such as a centrifuge, is necessary, except for magnetic nanoparticles and a magnet.

DESCRIPTION OF DRAWINGS

FIG. 6 is a conceptual illustration of separation using magnetic nanoparticles and a pipette.

BEST MODE

A better understanding of the present invention may be obtained through the following examples which are set forth to illustrate, but are not to be construed as limiting the present invention. Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Figure 1:
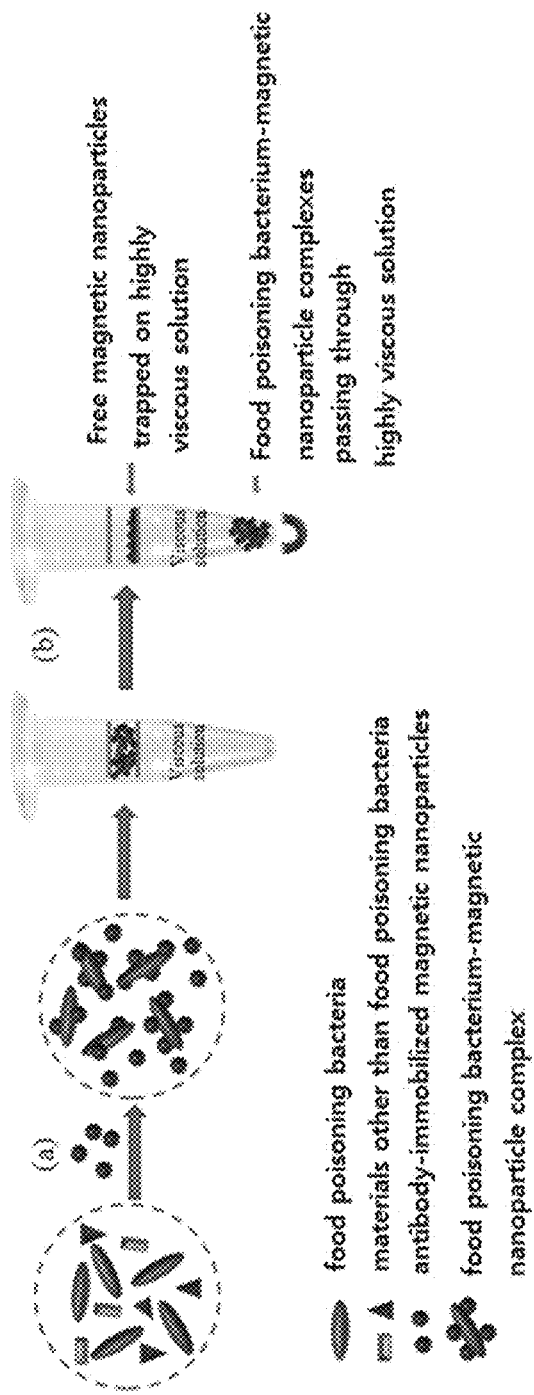
FIG. 1 is a schematic illustration of (a) the enrichment of food poisoning bacteria using magnetic nanoparticles and (b) the separation of food poisoning bacterium-magnetic nanoparticle complexes using a magnet.
Figure 2:
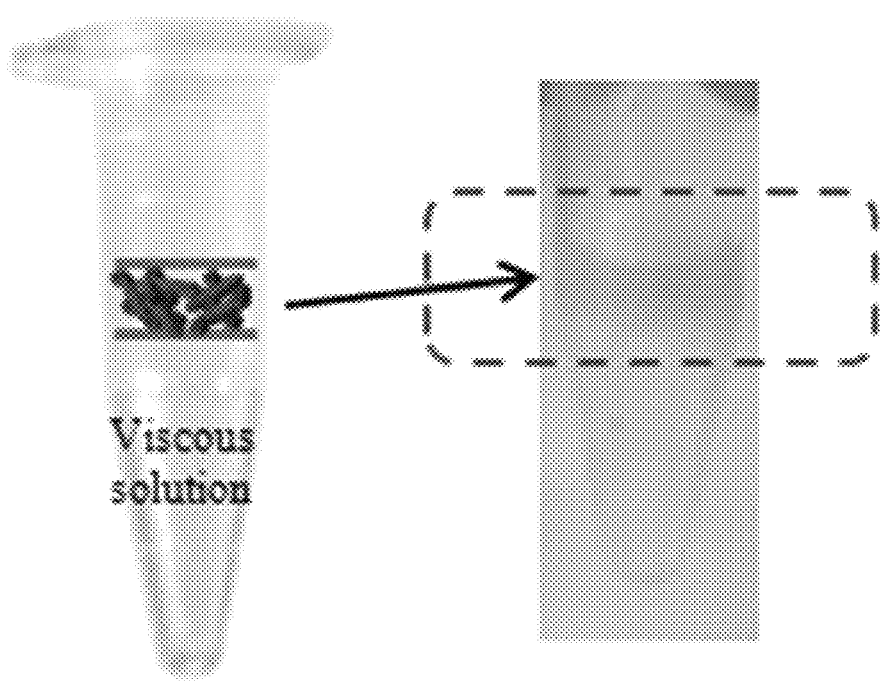
FIG. 2 shows a schematic view of a mixture of food poisoning bacterium-complexed magnetic nanoparticles and free magnetic nanoparticles placed on a highly viscous liquid, and a corresponding optical image thereof.
Figure 3:
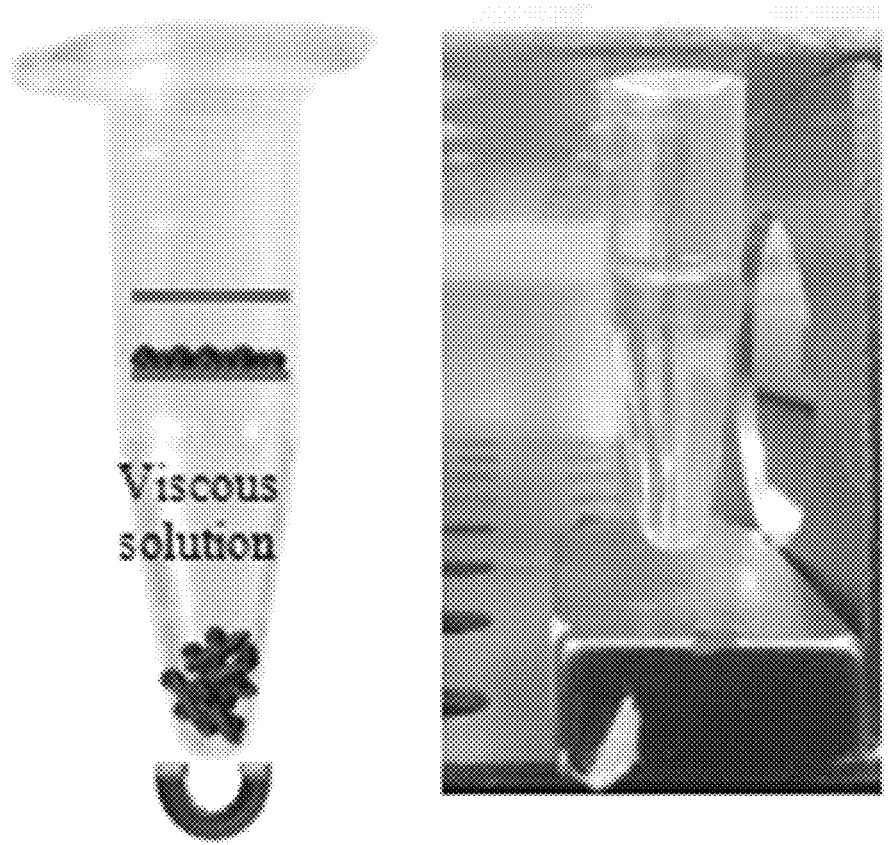
FIG. 3 shows a schematic view of the separation between food poisoning bacterium-complexed magnetic nanoparticles and free magnetic nanoparticles, and a corresponding optical image thereof.
Figure 4:
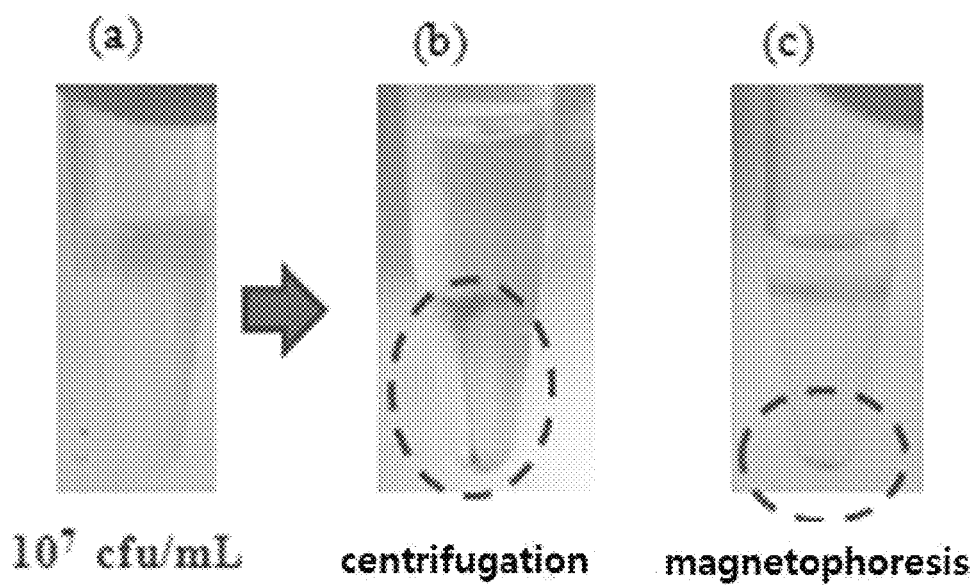
FIG. 4 shows optical images before (a) and after food poisoning bacterium-complexed magnetic nanoparticles and free magnetic nanoparticles are separated in a highly viscous medium by centrifugation (b) or by magnetism (c).
Figure 5:
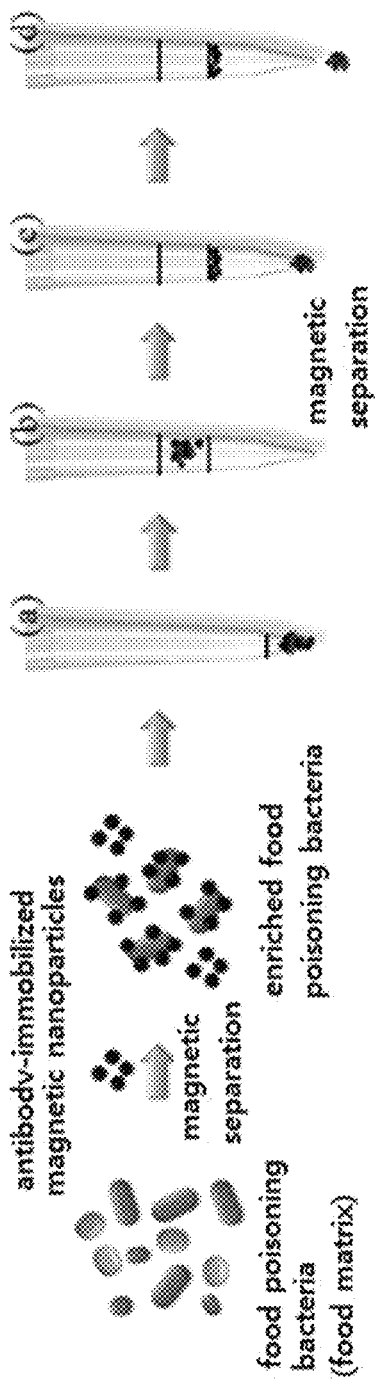
FIGS. 5A and 5B show UV-Vis absorbance profiles of separated food poisoning bacterium-magnetic nanoparticle complexes (a), and the mean absorbance at 593.68 nm of separated food poisoning bacterium-magnetic nanoparticle complexes by bacterial concentration, with the log concentration of food poisoning bacteria on the X axis (b).
Figure 7A:
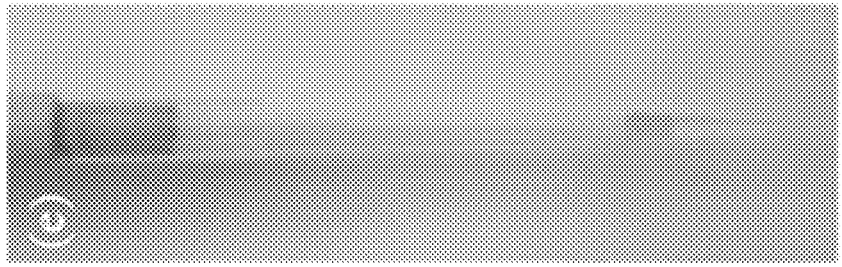
FIG. 7 shows food poisoning bacterium-magnetic nanoparticle complexes and free magnetic nanoparticles in a pipette tip in an corresponding optical image after separation; (a) before separation; (b) after separation (food poisoning bacteria absent); (c) in a magnified image of (b); (d) after separation (food poisoning bacteria present); and (e) in a magnified image of (d).
Figure 7B:
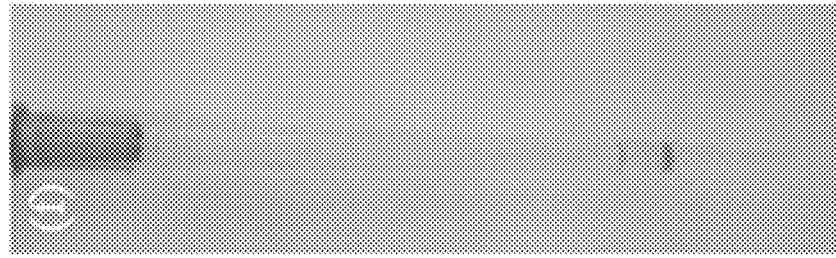
Figure 7C:
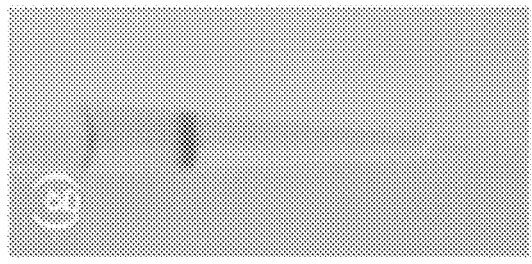
Figure 7D:
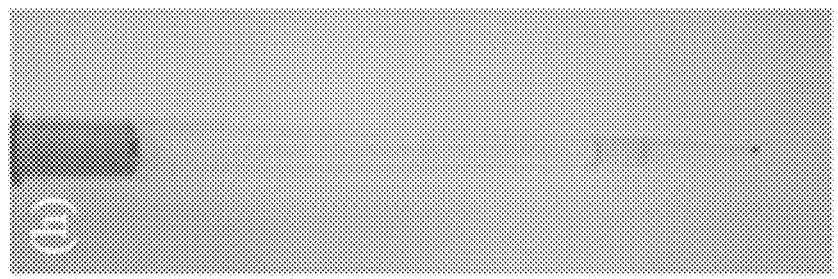
Figure 7E:
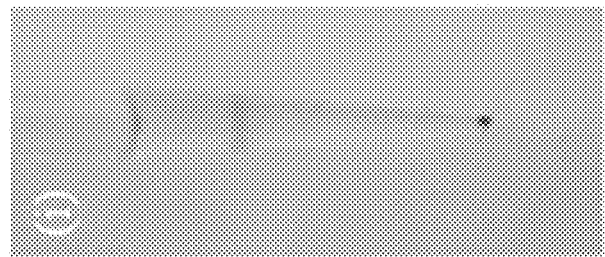

FIG. 1 is a schematic illustration of (a) the enrichment of food poisoning bacteria using magnetic nanoparticles and (b) the separation of food poisoning bacterium-magnetic nanoparticle complexes using a magnet; FIG. 2 shows a schematic view of a mixture of food poisoning bacterium-complexed magnetic nanoparticles and free magnetic nanoparticles placed on a highly viscous liquid, and a corresponding optical image thereof; FIG. 3 shows a schematic view of the separation between food poisoning bacterium-complexed magnetic nanoparticles and free magnetic nanoparticles, and a corresponding optical image thereof; FIG. 4 shows optical images before (a) and after food poisoning bacterium-complexed magnetic nanoparticles and free magnetic nanoparticles are separated in a highly viscous medium by centrifugation (b) or by magnetism (c); and FIGS. 5A and 5B show UV-Vis absorbance profiles of separated food poisoning bacterium-magnetic nanoparticle complexes (FIG. 5A), and the mean absorbance at 593.68 nm of separated food poisoning bacterium-magnetic nanoparticle complexes by bacterial concentration (FIG. 5B).

1. Reagents and Instruments

Iron(III) chloride ($FeCl_3$), urea, sodium citrate, polyacrylamide, 3-aminopropyl triethoxysilane (APTES), glutaraldehyde, and bovine serum albumin (BSA) were purchased from Sigma-Aldrich. Polyethylene glycol was purchased from Fluka. An antibody to food poisoning bacteria was purchased from Abcam Inc. Deionized water was obtained using a reverse osmosis water purification system (Human Science, Korea), and was used in synthesizing magnetic nanoparticle clusters and preparing a phosphate buffer. The neodymium magnet used in enriching and separating food poisoning bacterium-complexed magnetic nanoparticles was purchased from Seoul Magnet, and was observed to have a magnetic intensity of 30 mT. Quantification of separated food poisoning bacterium-magnetic nanoparticle complexes was carried out by measuring absorbance in a UV-Vis spectrometer from Ocean Optics.

2. Synthesis of $Fe_3O_4$ Magnetic Nanoparticle Cluster (Hereinafter Referred to Just as "Magnetic Particles") and Antibody Immobilization $Fe_3O_4$ magnetic nanoparticles were synthesized using a one-pot solvothermal method. Briefly, 4 mmoles of iron chloride, 12 mmoles of urea, and 8 mmoles of sodium citrate were dissolved together in 80 mL of water. Then, 0.6 g of polyacrylamide was added to the solution while stirring with the aid of a magnetic bar. The resulting solution was maintained at 200° C. in a 10 mL Teflon-lined autoclave container for 12 hrs to conduct a synthetic reaction. After the solution was cooled to room temperature, the particles thus synthesized were collected using a magnet while the remainder was removed. Then, the particles were rinsed several times with water and absolute ethanol to afford $Fe_3O_4$ magnetic nanoparticles. The nanoparticles were about 200 nanometers in size.

The synthesized magnetic nanoparticles were sequentially treated with APTES and glutaraldehyde to form on the surface thereof amine groups that could be coupled with an antibody. Thereafter, an antibody and magnetic nanoparticles were mixed to allow the antibody to be immobilized on the surface of the particles, and blocked with BSA to prevent the antibody from non-specific binding.

3. Preparation of Highly Viscous Medium

In this experiment, polyethylene glycol having a molecular weight of 8000 was dissolved in an amount of 30 wt % in water to give a highly viscous solution. This solution was measured to have a viscosity of about 50 mPa·s, which is about 50-fold higher than that (0.89 mPa·s) of water.

4. Detection of Food Poisoning Bacteria

This test was conducted against Salmonella [Salmonella typhimurium]. The food poisoning bacteria in a solution was incubated with the antibody-immobilized magnetic nanoparticles to allow the bacteria to complex with the nanoparticles. Then, magnetic nanoparticles were enriched using a magnet. The enriched particles were dispersed in a buffer and placed on a highly viscous solution. By bringing a neodymium magnet underneath the solution, food poisoning bacterium-complexed magnetic nanoparticles were separated from free magnetic nanoparticles.

In this regard, a layer of free magnetic nanoparticles was formed in an upper position in the solution while the food poisoning bacterium-complexed magnetic nanoparticles moved downward to the bottom. Hence, the food poisoning bacterium-complexed magnetic nanoparticles were obtained by first removing the upper free magnetic nanoparticles. The food poisoning bacterium-complexed magnetic nanoparticles were observed to have a size of about 3~4 micrometers as measured by dynamic light scattering.

The separated food poisoning bacterium-complexed magnetic nanoparticles were concentrated into a volume of 100 microliters, and the absorbance thereof was measured in order to detect the food poisoning bacteria.

Comparative Example

The same procedure as in the above Example was repeated, with the exception that the separation was achieved by centrifugation, instead of the use of a pipette tube. As can be seen in FIG. 4, the magnetic nanoparticles were distributed from a top position to a bottom position, like a continuous strip. Thus, it was difficult to separate bacterium-complexed magnetic nanoparticles from free magnetic nanoparticles.

Example 2

A mixture of food poisoning bacterium-complexed magnetic nanoparticles and free magnetic nanoparticles was obtained in the same manner as in 1. Reagents and Instruments, 2. Synthesis of $Fe_3O_4$ magnetic nanoparticle cluster and Antibody Immobilization, and 3. Preparation of Highly Viscous Medium of Example 1.

The mixture was sucked into a pipette tip by pipetting, as shown in FIG. 6 item a. Then, the pipette tip was immersed in the highly viscous solution, and a desired volume of the highly viscous solution was introduced into the pipette tip by rotating the volume adjusting wheel of the pipette so that the mixture was positioned on the highly viscous solution, as shown in FIGS. 6 item b and 7A.

Next, while the tip remained fitted into the pipette, the tip was positioned on a magnet until the food poisoning bacterium-complexed magnetic nanoparticles traversed the highly viscous solution and gathered at the end of the tip, as shown in FIGS. 6 item c and 7D.

Finally, the food poisoning bacterium-complexed magnetic nanoparticles gathered at the end of the tip were released out of the tip by rotating the volume adjusting wheel of the pipette, as shown in FIG. 6 item d.

The invention claimed is:

1. A method for quantitatively analyzing bacteria in a sample, comprising:
    introducing magnetic nanoparticles capable of capturing bacteria into the sample and allowing the magnetic nanoparticles to capture bacteria;
    separating the magnetic nanoparticles from the sample;
    passing the separated magnetic nanoparticles through a highly viscous medium in presence of a magnetic field to separate the magnetic nanoparticles into bacterium-complexed magnetic nanoparticles and free magnetic nanoparticles wherein the highly viscous medium is 10- to 1,000-fold higher in viscosity than water and the highly viscous medium is an aqueous solution containing polyvinylpyrrolidone in an amount of 10~50 weight % or polyethylene glycol solution, and the size of the bacterium-complexed magnetic nanoparticles are bigger than the free magnetic nanoparticles; and
    quantitating the bacterium-complexed magnetic nanoparticles.

2. The method of claim 1, wherein the magnetic nanoparticles range in size from 100 to 500 nanometers.

3. The method of claim 1, wherein the magnetic nanoparticle is conjugated on a surface thereof with an antigen derived from the bacteria.

4. The method of claim 1, wherein at least one of the magnetic nanoparticles binds to each of the bacteria.

5. The method of claim 1, wherein the bacteria are food poisoning bacteria.

6. The method of claim 5, wherein the food poisoning bacteria are selected from the group consisting of *Salmonella, Staphylococcus, Vibrio, Listeria*, pathogenic *E. coli*, enterohemorrhagic *E. coli* O157, *Campylobacter, Bacillus cereus, Clostridium welchii, Botulinus*, and a combination thereof.

7. The method of claim 1, the highly viscous medium is higher in viscosity than water.

8. The method of claim 1, wherein the highly viscous medium is a polymer solution.

9. The method of claim 1, wherein the passing step is carried out by placing the enriched magnetic nanoparticles on the highly viscous medium and allowing the magnetic nanoparticles to run downward through the highly viscous medium beneath which a magnet is positioned.

10. The method of claim 1, wherein the bacteria are quantitatively analyzed using UV-Vis absorbance.

11. A method for measuring bacteria comprising inducing bacterium-complexed magnetic nanoparticles and free magnetic nanoparticles to traverse a highly viscous solution by magnetism wherein the solution has a viscosity 10- to 1,000-fold higher in viscosity than water, and separating the bacterium-complexed magnetic nanoparticles and free magnetic nanoparticles from each other and measuring the bacterium-complexed magnetic nanoparticles.

12. A method for separating bacteria, comprising sucking a mixture of bacterium-complexed magnetic nanoparticles and free magnetic nanoparticles into a pipette tip; introducing a highly viscous medium into the pipette tip wherein the medium has a viscosity 10- to 1,000-fold higher in viscosity than water; standing the pipette tip on a magnet; and releasing the magnetic nanoparticles from the pipette tip.

13. The method of claim 12, wherein the pipette tip is allowed to stand on the magnet while the pipette tip is fitted into a pipette.

* * * * *